US009879360B2

(12) United States Patent
Delamarche et al.

(10) Patent No.: US 9,879,360 B2
(45) Date of Patent: *Jan. 30, 2018

(54) MICROFLUIDIC SELECTION OF LIBRARY ELEMENTS (75) Inventors: Emmanuel Delamarche, Thalwil (CH); Robert Lovchik, Schoenenberg (CH); Daniel J. Solis, San Diego, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 335 days.

This patent is subject to a terminal disclaimer.

(21) Appl. No.: 12/143,272

(22) Filed: Jun. 20, 2008

(65) Prior Publication Data

US 2009/0318302 A1 Dec. 24, 2009

(51) Int. Cl.
*C12M 3/00* (2006.01)
*C40B 30/04* (2006.01)
*C40B 60/12* (2006.01)
*G01N 33/543* (2006.01)
*B01L 3/00* (2006.01)

(52) U.S. Cl.
CPC ........... *C40B 30/04* (2013.01); *B01L 3/5027* (2013.01); *C40B 60/12* (2013.01); *G01N 33/54366* (2013.01); *B01J 2219/0059* (2013.01); *B01J 2219/0074* (2013.01); *B01J 2219/00389* (2013.01); *B01J 2219/00418* (2013.01); *B01J 2219/00527* (2013.01); *B01J 2219/00585* (2013.01); *B01J 2219/00596* (2013.01); *B01J 2219/00605* (2013.01); *B01J 2219/00657* (2013.01); *B01J 2219/00659* (2013.01); *B01J 2219/00677* (2013.01); *B01J 2219/00702* (2013.01); *B01J 2219/00722* (2013.01); *B01J 2219/00725* (2013.01); *B01L 3/5025* (2013.01); *B01L 2300/087* (2013.01); *B01L 2300/0816* (2013.01); *B01L 2300/0864* (2013.01); *B01L 2400/0487* (2013.01); *B01L 2400/06* (2013.01)

(58) Field of Classification Search
None
See application file for complete search history.

(56) References Cited

U.S. PATENT DOCUMENTS

| 4,865,997 | A | 9/1989 | Stoker | |
|---|---|---|---|---|
| 6,272,939 | B1 * | 8/2001 | Frye | B01L 3/0203 73/864.81 |
| 6,451,191 | B1 | 9/2002 | Bentsen et al. | |
| 6,485,905 | B2 | 11/2002 | Hefti | |
| 7,785,782 | B2 * | 8/2010 | Chien et al. | 435/6.16 |
| 2002/0076825 | A1 * | 6/2002 | Cheng | B01L 3/502761 436/174 |
| 2002/0119482 | A1 * | 8/2002 | Nelson et al. | 435/6 |
| 2003/0008308 | A1 * | 1/2003 | Enzelberger | B01F 5/102 435/6.19 |
| 2003/0085126 | A1 | 5/2003 | Parce et al. | |
| 2004/0018611 | A1 * | 1/2004 | Ward | B82Y 15/00 435/287.2 |
| 2004/0048360 | A1 * | 3/2004 | Wada et al. | 435/287.2 |
| 2004/0146431 | A1 * | 7/2004 | Scherer | G01N 21/7746 422/82.05 |
| 2004/0185453 | A1 * | 9/2004 | Myerson et al. | 435/6 |
| 2004/0222180 | A1 * | 11/2004 | Wicks | B01L 3/50825 215/200 |
| 2004/0241733 | A1 | 12/2004 | Parce et al. | |
| 2005/0048561 | A1 * | 3/2005 | Fulwyler et al. | 435/6 |
| 2005/0109396 | A1 * | 5/2005 | Zucchelli | B01F 11/0002 137/67 |
| 2005/0176135 | A1 * | 8/2005 | Jones | B01L 3/502707 435/287.2 |
| 2005/0201901 | A1 * | 9/2005 | Grossman | B01L 3/502715 422/400 |
| 2005/0202504 | A1 * | 9/2005 | Anderson | B01F 11/0071 435/6.11 |
| 2007/0082408 | A1 * | 4/2007 | Jing | G01N 21/553 436/164 |
| 2007/0098600 | A1 * | 5/2007 | Kayyem | B01L 3/5027 422/400 |
| 2007/0231827 | A1 * | 10/2007 | Zhang | 435/7.1 |
| 2008/0014575 | A1 * | 1/2008 | Nelson | G01N 33/54306 435/5 |
| 2008/0277387 | A1 | 11/2008 | Landers et al. | |
| 2009/0318303 | A1 * | 12/2009 | Delamarche | B01L 3/502707 506/9 |
| 2011/0166027 | A1 * | 7/2011 | Weiner | 506/4 |

FOREIGN PATENT DOCUMENTS

| EP | 1415788 A1 | 5/2004 |
|---|---|---|
| EP | 1867733 A1 | 12/2007 |
| WO | 2005095262 A1 | 10/2005 |

OTHER PUBLICATIONS

Teuro Fujii; "PDMS-based microfluidic devices for biomedical applications;" Microelectronic Engineering 61-62; 2002; pp. 907-914.

(Continued)

*Primary Examiner* — Ann Lam (74) *Attorney, Agent, or Firm* — Thomas A. Beck; Daniel P. Morris (57) ABSTRACT

Disclosed herein is a microfluidic device comprising a chip; a flow channel being disposed in the chip; the flow channel being in communication with an entry port and an exit port; the flow channel being operative to permit the flow of a library from the entry port to the exit port; a substrate; the substrate being disposed upon the chip; the substrate being operative to act as an upper wall for the flow channels; and a plurality of receptors; the plurality of receptors being disposed on the substrate; the plurality of receptors being operative to interact with an element from the library.

4 Claims, 5 Drawing Sheets

(56) References Cited

OTHER PUBLICATIONS

International Search Report; International Application No. PCT/IB2009/052644; dated Nov. 4, 2009; 4 pages.
A. Visser, "Towards Sorting of Biolibraries Using Single-Molecule Fluorescence Detection Techniques". Current Pharmaceutical Biotechnology (2004) vol. 5, pp. 173-179. Bentham Science Publishers, Ltd.
E. Delamarche, et al. "Microfluidics for Processing Surfaces and Miniaturizing Biological Assays". Advanced Materials (2005) vol. 17, pp. 2911-2933. Wiley-VCH, Verlag GmbH & Co., Weinheim.
P. Bessette, et al. "Microfluidic Library Screening for Mapping Antibody Epitopes". Analytical Chemistry (Mar. 1, 2007) vol. 79, No. 5, pp. 2174-2178. American Chemical Society.

\* cited by examiner

MICROFLUIDIC SELECTION OF LIBRARY ELEMENTS

BACKGROUND

This disclosure relates to the microfluidic selection of library elements.

It is desirable in virtually every area of the biomedical sciences to have systems that are based on chemical or biochemical assays for determining the presence and quantity of particular analytes. This desire ranges from the basic science research lab, where biochemical pathways are being mapped out and their functions correlated to disease processes, to clinical diagnostics, where patients are routinely monitored for levels of clinically relevant analytes. Other areas include pharmaceutical research and drug discovery applications, DNA testing, veterinary, food, and environmental applications. In all of these cases, the presence and quantity of a specific analyte or group of analytes, has to be determined.

For analysis in the fields of pharmacology, genetics, chemistry, biochemistry, biotechnology, molecular biology and others, it is often useful to detect the presence of one or more molecular structures and characterize interactions between molecular structures. The molecular structures of interest generally include antibodies, antigens, metabolites, proteins, drugs, small molecules, enzymes, nucleic acids, and other ligands and analytes. The molecular structures can also be inside or outside cells and microorganisms. In medicine, for example, it is very useful to determine the existence of cellular constituents such as receptors or cytokines, or antibodies and antigens which serve as markers for various disease processes, which exist naturally in physiological fluids or which have been introduced into the system. In genetic analyses, fragment DNA and RNA sequence analysis are very useful in diagnostics, genetic testing and research, agriculture, and pharmaceutical development. Because of the rapidly advancing state of molecular cell biology and understanding of normal and diseased systems, there always exists an increasing need for newer, more rapid, and more accurate methods of detection.

A useful technique for the identification of such molecular structures as well as interactions between molecular structures is high throughput screening of large collections of chemicals or biochemicals, often referred to as "libraries". Most high-throughput screens measure the action of compounds on a single molecular phenomenon, e.g., a particular enzymatic activity that is thought to play a role in some physiological system such as a disease state. Prior to the screening process, the elements of such libraries have not been demonstrated to have action on the molecular phenomenon measured by the screen or the disease state in which the molecular phenomena plays a role. Such a screen is designed to identify compounds that affect that particular molecular phenomenon, so that the physiological system in which the phenomenon plays a role may be impinged upon with the identified compounds.

Screening of libraries is often conducted by using microtiter plates and bead based screening. In screening a library using a microtiter plate, a microtiter plate well is coated with a target of interest (e.g., a receptor). Bacteriophage libraries, more commonly called phage libraries, are often used for screening purposes. In these libraries, chemical variability is introduced in the genome of the phages and because a large number of phages can be contained in a small volume of library, large chemical diversity in the phages can be achieved. In the phage libraries, the variable part of the genome of a phage can be expressed and displayed as a coat protein. Therefore, screening a phage library can be accomplished by looking for interactions between a receptor of interest and a particular protein displayed on the surface of the phage. A phage library is then placed in contact with a well of an analytical device that contains a receptor of interest. Some of the phages bind to the receptor. The well is then washed to remove those phages that are not bound to the receptor. After removal of the unbound phages, those phages that are bound to the receptor are eluted. The DNA of some of the bound phages is then sequenced to assess the quality of the screening. The eluted phages are then copied to increase their numbers (amplification). The foregoing steps are then repeated until the genetic sequences of the bound phages show "consensus". The emergence of a consensus shows that screening has resulted in extracting from the library one or a few phages that are able to bind the receptor with equal probability.

In bead based screening, a bead of latex, silica, or other suitable material having an average particle size of about 1 to about 10 micrometers is coated with a receptor of interest. The phage library is allowed to interact with the beads freely in solution. Unbound phages and beads are separated using either centrifugation or particle sorting machines based on multiple technologies (magnetic bead, dielectrophoresis, fluorescence). Phages bound to the bead are eluted. As noted above, the eluted phages are subjected to amplification followed by the same series of steps described above to show consensus.

Because of the number of steps, both of the aforementioned methods involving microtiter plates and bead based screening are expensive, time consuming and labor intensive. For example, a phage library can cost around $1,000 to purchase and 2 to 4 rounds of screening generally take about 3 weeks. In addition, both of the above methods use multiple cycles, which opens the method to contamination as well as degradation in the quality of results.

The screening and identification of multiple elements from a library is even more difficult. While multiple elements can be screened simultaneously, information pertaining to the specificity of the interaction of the elements with each target is not easily obtained. For example, screening a library to find logical binders, i.e., a binder that binds to a first target and a second target, a first target or a second target, or a first target but not a second target is very difficult and compounds the complexity of the screening work. In other words, screening a library to find a binder for the first target and the second target uses more than twice the work of screening against the first target followed by screening against the second target.

It is therefore desirable to have a method that can be used for screening phage libraries efficiently and inexpensively.

SUMMARY

Disclosed herein is a microfluidic device comprising a chip; a plurality of flow channels being disposed in the chip; the plurality of flow channels being in communication with an entry port and an exit port; the plurality of flow channels being operative to permit the flow of a library from the entry port to the exit port; a substrate; the substrate being disposed upon the chip; the substrate being operative to act as an upper wall for the plurality of flow channels; and a receptor; the receptor being disposed on the substrate; the receptor being operative to interact with an element from the library.

Disclosed herein too is a microfluidic device comprising a chip; a flow channel being disposed in the chip; the flow channel being in communication with an entry port and an exit port; the flow channel being operative to permit the flow of a library from the entry port to the exit port; a substrate; the substrate being disposed upon the chip; the substrate being operative to act as an upper wall for the flow channels; and a plurality of receptors; the plurality of receptors being disposed on the substrate; the plurality of receptors being operative to interact with an element from the library.

Disclosed herein too is a method comprising disposing a library on a loading pad of a microfluidic device; the microfluidic device comprising a chip; a plurality of flow channels being disposed in the chip; the plurality of flow channels being in communication with an entry port and an exit port; the plurality of flow channels being operative to permit the flow of a library from the entry port to the exit port; a substrate; the substrate being disposed upon the chip; the substrate being operative to act as an upper wall for the flow channel; and a plurality of receptors; the plurality of receptors being disposed on the substrate; the receptors being operative to interact with an element from the library; adding a first solution to the loading pad to transport elements of the library through the entry port into the flow channel; performing one of the following:

I) binding a fraction of the elements of the library to a first receptor of the plurality of receptors to form an element-receptor complex; and adding a second solution to the flow channel to cause a fraction of the element-receptor complexes to bind to a second receptor of the plurality of receptors thereby determining those elements of the library that can bind to the first receptor and to the second receptor; or II) binding a first fraction of the elements of the library to a first receptor of the plurality of receptors to form a first element-receptor complex; and binding a second fraction of the elements of the library to a second receptor of the plurality of receptors to form a second element-receptor complex; the second fraction of elements not being capable of forming the first element-receptor complex; or III) binding a first fraction of the elements of the library to a first receptor of the plurality of receptors to form a first set of element-receptor complexes; and binding a second fraction of the elements of the library to a second receptor of the plurality of receptors to form a second set of element-receptor complexes; the second fraction excluding the elements of the first fraction.

DETAILED DESCRIPTION

Disclosed herein is a system and a method for determining the identity of or the properties of elements from a library by using logical screening in conjunction with a microfluidic device. The elements of the library can be bacteriophages, viruses, self-assembled structures such as vesicles, or the like. The microfluidic devices that are used for logical screening advantageously provide a plurality of pathways (termed a "microfluidic network") by which a plurality of elements can be selected from a library or a plurality of libraries in a single pass through the microfluidic device.

In an exemplary embodiment, the microfluidic device comprises a plurality of flow channels, a plurality of receptors or a plurality of flow channels and a plurality of receptors. The screening of elements from a library is thus conducted by using a plurality of different types of receptors, by using a plurality of flow channels, or by using a combination of a plurality of channels and a plurality of receptors. The term plurality as used herein can mean "two or more".

The plurality of receptors are disposed in different areas of the substrate so that the receptor library element interaction can occur in well defined areas of the microfluidic device. This is important to ensure that different elements binding to different receptors do not get pooled when they are eluted and analyzed. The receptors can be from a similar class or from different classes. An example of similar classes is a case where a first element from a library binds to an antibody A disposed upon a first receptor, while a second element from the same library binds to an antibody B disposed upon a second receptor. The first receptor and the second receptor are contained in the same microfluidic network. An example of different classes is a case where a first element from a library binds to an antibody A disposed upon a first receptor, while a second element from the same library binds to a enzyme A disposed upon a second receptor. Once again, the first receptor and the second receptor are contained in the same microfluidic network.

As noted above, the microfluidic device can have a plurality of flow channels. The flow channels can be used to split a library and pass it over the same receptor. The plurality of flow channels can also be used to pass multiple libraries over the same receptor if desired.

In an exemplary embodiment, the system comprises a microfluidic network disposed upon a chip, wherein the fluid flow through the microfluidic network is controlled via valves. The valves can be located either on or off the chip. The design of the microfluidic network is such that when a library (that comprises bacteriophages, viruses, or the like—hereinafter termed "elements" of the library) is brought into contact with prepatterned areas of the microfluidic network, a target of interest located in the microfluidic network interacts with an element from the library. By increasing the number of such interactions between a single element and a receptor, a variety of complex interactions can be discovered in a single experiment.

As noted above, the microfluidic device comprises a plurality of flow channels that are in communication with an entry port and an exit port through which the library may be introduced and removed. The flow channel is further covered with a substrate that is coated with a plurality of receptors (also called targets); the receptors being selected for their ability to interact with a desired element or with desired elements from the library. Elements from the library react with the receptors during the transportation of the library through the flow channel. Following the reaction between the receptors and the element, non-bound elements can be removed by rinsing the flow channel, while the specific elements that react with the target can then be separated and analyzed.

In one embodiment, flow through the multiple channels is controlled via valves either that are disposed either on or off the chip (backpressure from the pump can be used to effectively shut of the channel). The design of the microfluidic network is such that the library is brought into contact with prepatterned areas comprising a target of interest in a manner such that complex binding solutions can be discovered in a single experiment.

The system is advantageous in that it can be used to rapidly analyze the library. Whereas 2 to 3 rounds of screening are generally used when using comparative microtiter plates, the present system and method permit a strong reduction of the library that can be achieved in only one round. The system permits flow conditions in the microfluidic channel to be controlled so that reaction parameters such as diffusion and kinetics of binding are shifted in favor of facilitating a desired reaction between specific library elements and the targets. Since the microfluidic channels have channel dimensions that are on the order of micrometers, the fluid flow in the channel is always laminar. This permits efficient rinsing and minimizes the presence and influence of dead volumes. As a result, the flow of solutions is precise in volume and rate of flow. In addition, the rinsing of the microfluidic device can be very efficient. The dynamics of reactions are dramatically affected by scale; controlling the dimensions and flow conditions of the flow channel can shift reaction parameters such as diffusion and kinetics of binding in favor of selection. Furthermore, microfluidic flow channels are closed systems and can be used to eliminate outside contamination.

Figure 1A:
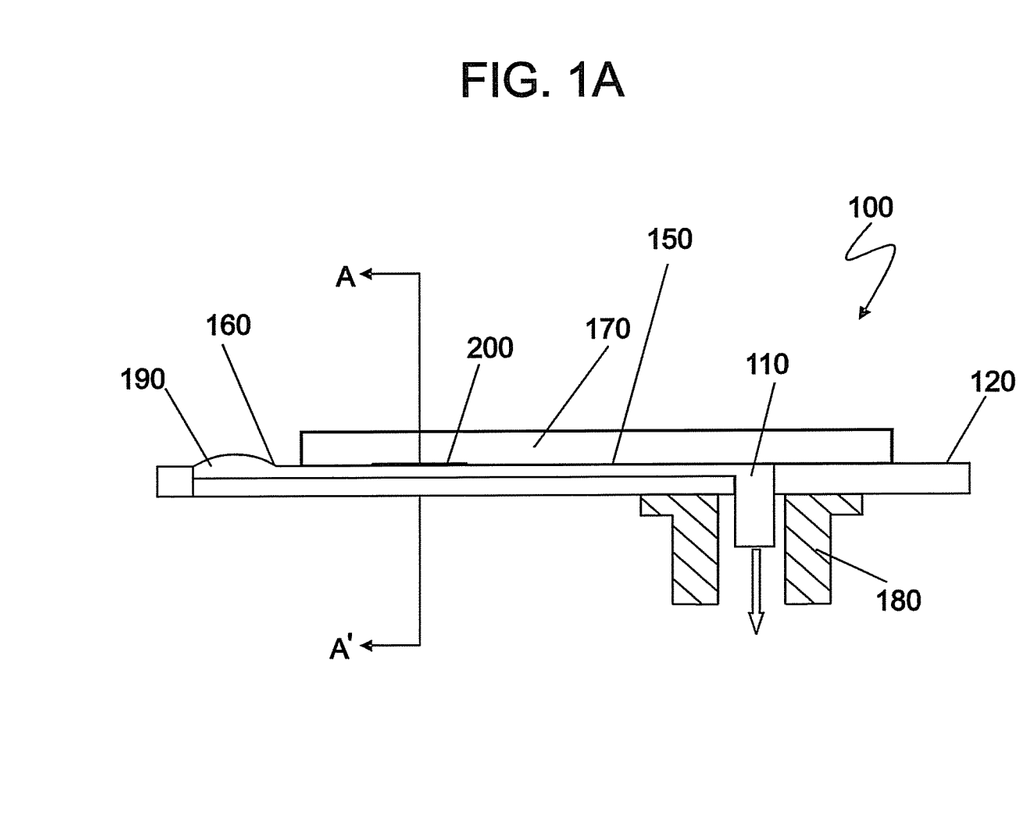
FIG. 1A is an exemplary depiction of the side view of the microfluidic device.
Figure 1B:
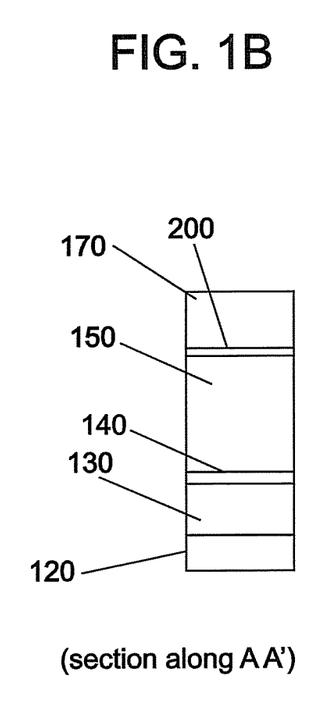
FIG. 1B is an exemplary depiction of a cross-sectional view taken at AA' of the microfluidic device depicted in the FIG. 1A.

With reference now to the FIGS. 1A and 1B, an exemplary micro fluidic device 100 comprises a chip 120 having an entry port 160, an exit port 110 and a flow channel 150 disposed therein. The flow channel 150 may have a linear path or a tortuous path between the entry port 160 and the exit port 110. FIG. 1A is a side view of the exemplary microfluidic device while FIG. 1B is a cross-sectional view of the microfluidic device taken at AA' of the FIG. 1A. The entry port 160 and the flow channel 150 are engraved in the chip 120. The entry port 160 is in communication with a loading pad 190, which is also engraved in the chip 120. The exit port 110 is engraved entirely through the chip and creates an opening on the face of the chip 120 that is opposed to the face upon which the flow channel 150 is disposed. The exit port 110 has a lip 180 disposed thereon. The lip 180 can be in fluid communication with an optional pump (not shown). A metal layer 130 is deposited upon the entire chip 120 or specifically on the engraved structures that come into contact with the library. These structures are the loading pad 190, the entry port 160, the flow channel 150, and the exit port 110. A passivation layer 140 can be disposed upon the metal layer 130 across the entire surface of the microfluidic device or only in the flow channel 150 if desired.

A substrate 170 is disposed upon the chip 120 and seals the flow channel 150, the entry port 160, and the exit port 110. The substrate should be in contact with the chip 120 so as to prevent the leakage of fluids. The substrate 170 may be manufactured from a suitable elastomer. A receptor 200 is disposed on the substrate 170. The receptor 200 is selected for its ability to interact with a desired element from a library. The receptor can be an enzyme, a peptide, a protein, inorganic particles, beads coated with a receptor, uncoated beads, cells, glycans, viral particles, polymers, antibodies, antigens or other type of molecule or material that can have a ligand-receptor type of interaction with proteins or peptides displayed by bacteriophages. The receptor can for example be patterned on the substrate surface using stencils, inkjet deposition methods or other methods for patterning proteins on surfaces. Alternatively, the receptor can be deposited onto the substrate by flowing a solution of a receptor in the flow channel 150 after it is sealed with the substrate 170.

A first solution is added to the loading pad 190 to transport the bacteriophages through the entry port 160 into the flow channel 150. Once in the flow channel 150, the bacteriophages encounter the receptor. Binding occurs between selected bacteriophages and the receptor, depending upon the choice of the receptor. The first solution in the flow channel 150 can then be pumped out using the pump that is in fluid communication with the lip. In another embodiment, the first solution in the flow channel can be forced out of the flow channel using capillarity. In yet another embodiment, an amount of washing solution can be introduced into the flow channel to displace the previously introduced first solution from the flow channel.

After removing the first solution from the flow channel by washing, an elution solution is added to the flow channel via the loading pad and the entry port to elute the bacteriophages, which are bound to receptors disposed upon the substrate 170. The goal of the elution step is to separate the phages from the receptors so as to retrieve them for analysis using conventional methods based on, for example, DNA sequencing. Alternatively, some characteristics of the phage-receptor binding interaction can be analyzed before the elution step. These interactions can be investigated using radioactivity, fluorescence, chemiluminescence, phosphorescence, enzymatic activity, micro-calorimetry, mass-spectroscopy, or the like. Typically, eluted phages are multiplied using bacterial hosts to amplify their number and make them more convenient to handle and analyze.

While the FIGS. 1A and 1B are exemplary embodiments that depict only a single flow channel having a single receptor, the remaining embodiments are directed to microfluidic devices 100 that comprise a plurality of flow channels and/or a plurality of receptors. It is to be noted that when the microfluidic device comprises a plurality of flow channels, the plurality of flow channels will be connected to an entry port and one exit port. The plurality of flow channels are operative to permit the flow of a library from the entry port to the exit port.

Figure 2A:
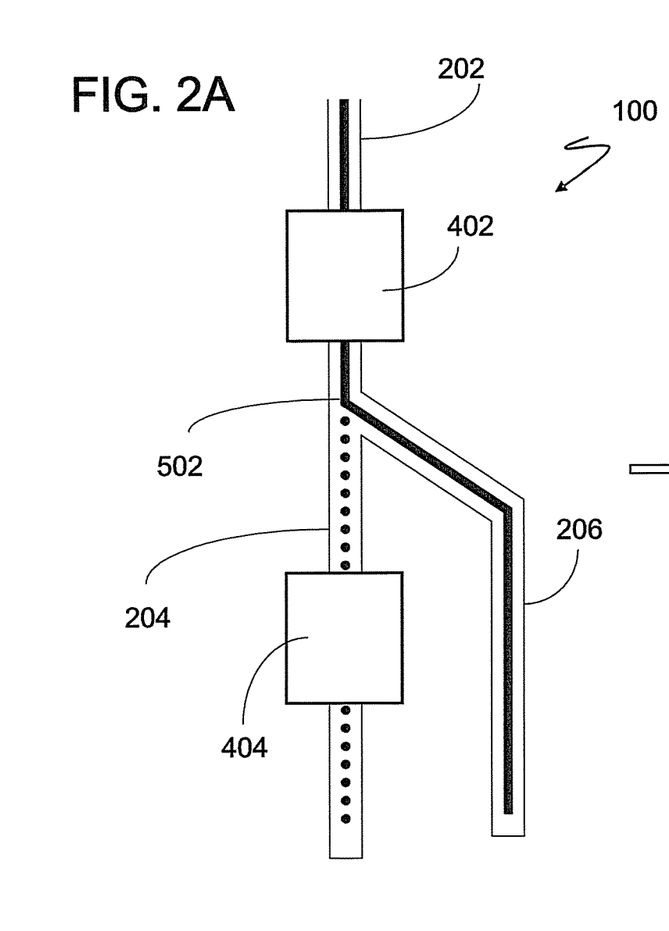
FIGS. 2A and 2B depict one embodiment of operating the microfluidic device so as to detect elements of a library that can bind to a first receptor and (AND) to a second receptor.
Figure 2B:
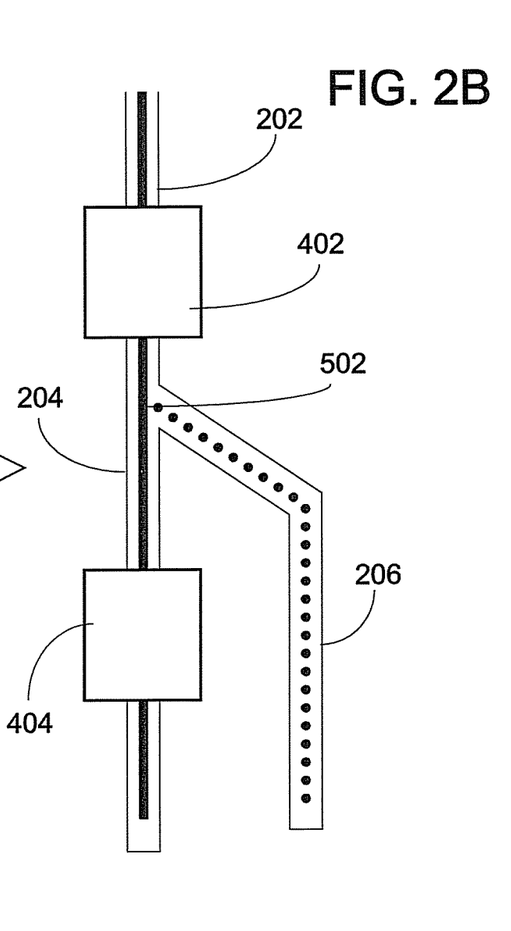

FIGS. 2A and 2B depict one exemplary embodiment of the microfluidic device 100 that is set up to detect elements of a library that can bind to a first receptor as well as to a second receptor. Since the microfluidic device 100 is used to screen elements of the library that can bind to a plurality of receptors, it is said to operate in the "AND" mode. The FIGS. 2A and 2B are depictions of an exemplary embodiment of the microfluidic device 100 that comprises a plurality of flow channels—a first flow channel 202, a second flow channel 204 and a third flow channel 206 respectively. The second flow channel 204 and the third flow channel 206 are in fluid communication with the first flow channel 202. The second flow channel 204 and the third flow channel 206 are branches of the first flow channel 202 and are formed at a first junction 502. Additional fluid channels such as, for example, a fourth flow channel (not shown), a fifth flow channel (not shown), and so on, may be provided. These additional channels can serve as branches that are in fluid communication with the first flow channel 202 in a manner similar to that depicted for the second flow channel 204 and the third flow channel 206. The additional channels described above can form branches at the first junction or at a second junction or a third junction (not shown) if desired. In the FIGS. 2A and 2B, the second flow channel 204 and the third flow channel 206 are located downstream of the first flow channel 202. The arrangement of the plurality of channels depicted in the FIGS. 2A and 2B are termed the "microfluidic network". The flow through the respective flow channels can be controlled by valves (not shown) that are disposed on the chip or off the chip. In one embodiment, when valves are disposed off the chip, a back pressure can be used to prevent the flow of a solution through a particular flow channel.

A first receptor 402 and a second receptor 404 are disposed on the substrate 170 that is disposed on the chip. The first receptor 402 is disposed on the first flow channel 202, while the second receptor 404 is disposed on the second flow channel 204.

A library of bacteriophages can be tested against the first receptor 402. While the method disclosed herein describes the use of library of bacteriophages, other libraries comprising viruses, self assembled molecules, or the like, may also be used.

In one embodiment, in one manner of using the microfluidic device 100 to screen a library, a library is screened against the first receptor 402. Some elements of the library can bind to the first receptor 402 to form an element-receptor complex, while the non-binding elements are diverted at the first junction 502 to third flow channel 206. The non-binding elements passing through to a waste disposal as to never interact with the second receptor 404. The discharge of the non-binding elements from the first flow channel 202 to the third flow channel 206 can be accomplished by a pump (not shown). The pump is used to discharge a first solution through the first flow channel 202. The first solution carries all non-binding elements with it to the third flow channel 206.

A second solution is then passed through the first flow channel 202 to elute the element-receptor complex (i.e., elements of the library bound to first receptor 402), but this time the eluted elements are directed towards the second receptor 404. The elements that are bound to the first receptor 402 but not to the second receptor 404 are not retained. However, those elements that are bound to both the receptors 402 and 404 are immobilized and retained on the second receptor 404.

In other words, a fraction of the element-receptor complexes that bond to the first receptor 402 will also bond to the second receptor 404. The element-receptor complexes that bond to both the first receptor 402 and the second receptor 404 are eluted and analyzed. Thus elements demonstrating a high affinity for the first receptor 402 are also interacted with the second receptor 404 to determine affinity. Because these element-receptor complexes have very specific interactions, it is possible to specifically elute elements that bind to the first receptor 402 without compromising the binding of these elements to the second receptor 404. This can be accomplished, for example, by eluting bound elements using a chemical known to bind and compete for one of the receptors. Alternatively, changing the pH, salt concentration, amount of surfactant, or changing the temperature can be used to elute elements from one type of receptor without compromising the binding of the elements to the other type of receptor. Thus by operating the system in the aforementioned configuration, the various elements of the library can be identified based on their ability to interact and bind to two or more different types of receptors.

Figure 3A:
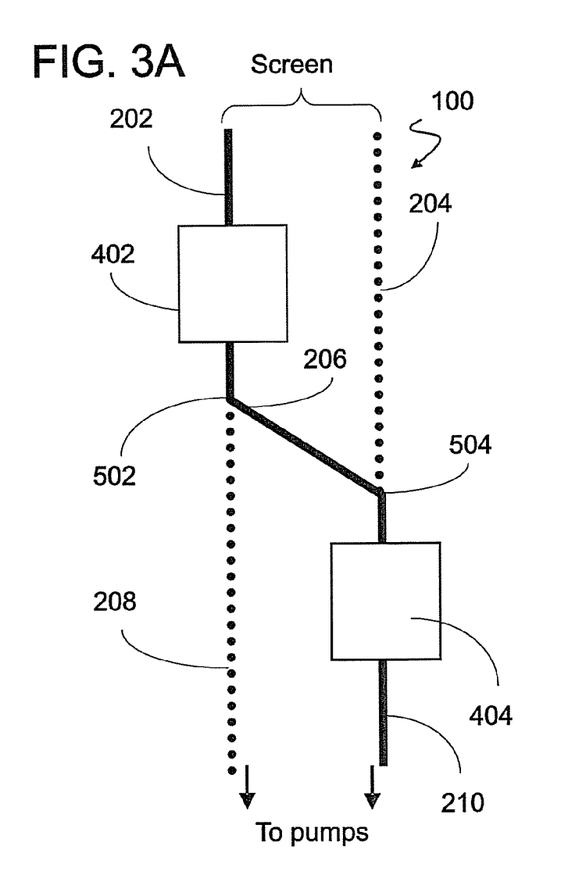
FIGS. 3A and 3B depict another mode of operating the microfluidic device so as to detect elements of a library that can bind to a first receptor but not (NOT) to a second receptor.
Figure 3B:
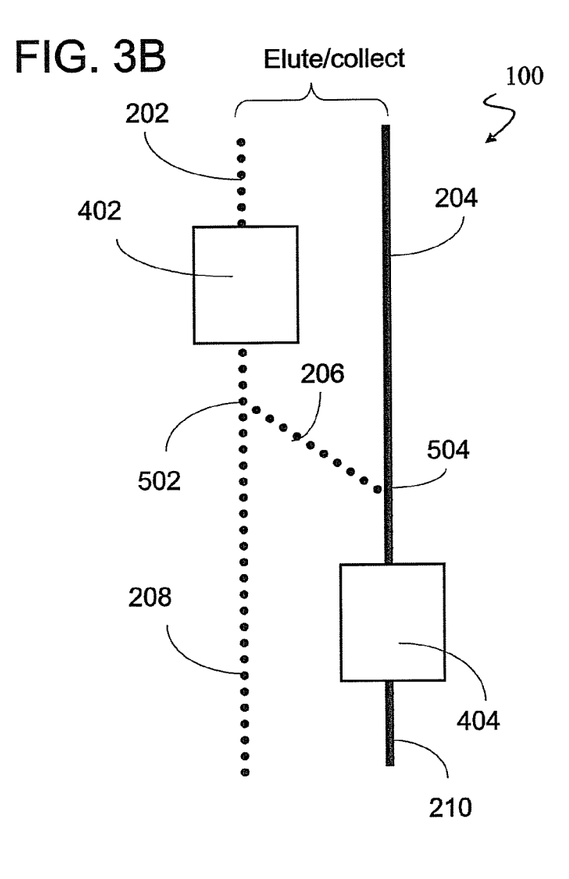

FIGS. 3A and 3B depict another mode of operating the microfluidic device 100 so as to detect elements of a library that can bind to a first receptor but not to a second receptor. The elements that bond to the first receptor will not have an opportunity to bond to the second receptor. The microfluidic device 100 is therefore said to operate in the "NOT" mode. Other elements of the library that have not bonded to the first receptor can bond to the second receptor. In the embodiment depicted in the FIGS. 3A and 3B, the chip has two receptors, a first receptor 402 and a second receptor 404 and five flow channels 202, 204, 206, 208 and 210 respectively. The receptors 402 and 404 are patterned at their respective surfaces. The first receptor 402 is disposed upon the first flow channel 202, while the second receptor 404 is disposed upon the fifth flow channel 210. As can be seen in the FIGS. 3A and 3B, the second flow channel 204, the third flow channel 206 and the fourth flow channel 208 do not have any receptors. The first flow channel 202, the third flow channel 206 and the fourth flow channel 208 are in fluid communication with each other and meet at the first junction 502.

The second flow channel 204, the third flow channel 206, the fourth flow channel 208 and the fifth flow channel 210 are each downstream of the first flow channel 202. The third flow channel 206, the second flow channel 204 and the fifth flow channel 210 are also in fluid communication with one another and meet at the second junction 504. As noted above, the flow through the respective flow channels can be controlled by valves (not shown) that are disposed on the chip or off the chip. In general, valves located at the first junction 502 and the second junction 504 are used to prevent elements that are bound to the first receptor 402 from interacting with the second receptor 404. This prevents any cross-talk between the elements or solutions in the first flow channel 202 and those in the second flow channel 210.

In one embodiment, in one manner of operation of the microfluidic network shown in the FIGS. 3A and 3B, a library is screened by passing it through the first flow channel 202. A first fraction of the elements of the library interact and bind with the first receptor 402 to form a first element-receptor complex. The library is retained in the vicinity of the receptor 402 for an extensive period of time to enable all elements capable of interacting with the receptor 402 to form the first element-receptor complexes. The elements that do not bind to the first receptor 402 are discharged to the first junction 502 from where they travel to the fifth flow channel 210 to interact with the second receptor 404. Upon interacting with the second receptor 404, a second fraction of the elements from the library bind with the second receptor 404 to form a second element-receptor complex. Valves (not shown) can be used to prevent the travel of the elements to flow channels 208 and 204. The elements of the library are retained in the vicinity of the receptor 404 for a period of time sufficient to enable those elements capable of binding to the receptor 404 to do so.

Following this the elements bound to the receptor 402 are eluted through the flow channel 208. During the elution of these elements, valves (not shown) prevent the travel of the eluate through the third flow channel 206, thus preventing the interaction of elements that had previously bonded to the receptor 402 from interacting with the receptor 404. The elements bound to the receptor 404 are then eluted through the fifth flow channel 210. During the elution of the elements that are bound to the receptor 404, the valves (not shown) are shut to prevent any interaction of these elements with the receptor 402. Thus the eluate obtained at the channel 210 contains only those elements that can bind with the receptor 404 but not to the receptor 402. Thus by operating the system in the aforementioned configuration, the various elements of the library can be identified based on their ability to interact exclusively with different receptors.

In another embodiment, the microfluidic device 100 can be used to determine elements of the library that can bind with either a first receptor or a second receptor. With reference now to the FIG. 4, the library is split and interacts with two or more distinct, separate receptors. This type of screening differs from that shown above in FIGS. 2A and 2B, or 3A and 3B, in that the microfluidic device 100 can be used to detect those elements of a library that bind to either the first receptor or the second receptor. This type of screening is therefore referred to as "OR" screening. As can be seen in the FIG. 4, the microfluidic network 100 comprises a first flow channel 202 that splits into two flow channels—a second flow channel 204 and a third flow channel 206. The splitting into the two flow channels occurs at a first junction 502. The second flow channel 204 has a first receptor 402 disposed thereon while the third flow channel 206 has a second receptor 404 disposed thereon. The receptors are patterned on the surfaces that contact the elements of the library. The second and the third flow channels merge back into a single channel 208 downstream of the first and the second receptors. The merging of the second and the third flow channels into the single channel 208 occurs at the second junction 504.

Figure 4:
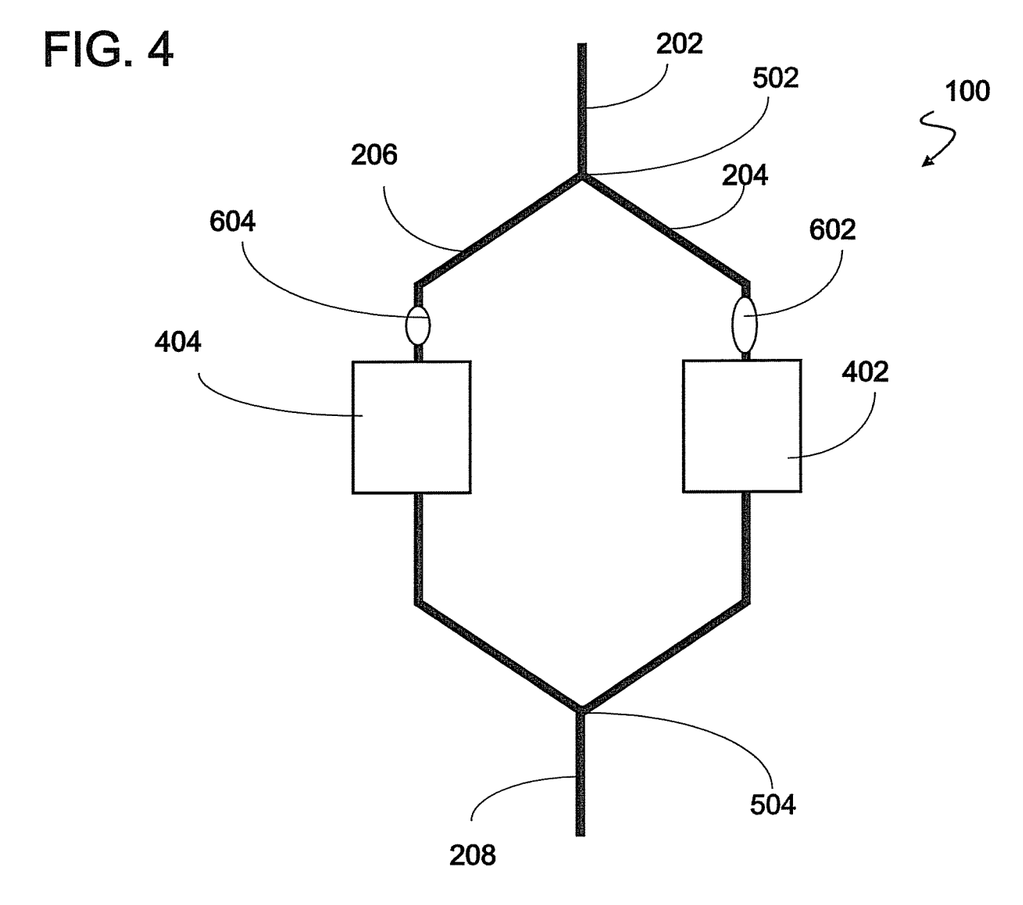
FIG. 4 is a depiction of one embodiment of the microfluidic device so as to detect elements of library that can bind to a first receptor or (OR) to a second receptor.

In one embodiment, in one manner of using the microfluidic device 100 depicted in the FIG. 4, a library is discharged into the first flow channel 202. The library is split at the junction 502, with roughly equal proportions the solution that carries the library being passed through the second flow channel 204 and the third flow channel 206. It is to be noted that flow-controlling devices 602 and 604 can be used to control the flow of the elements of the library to the respective receptors. By using the flow-controlling devices, a larger fraction of the library can be directed towards one of the receptors.

Elements of the library that pass through the second flow channel 204 will interact with the first receptor 402. A first fraction of these elements will bond to the first receptor 402 to form a first set or element-receptor complexes. A second fraction of the elements of the library that pass through the third flow channel 206 will interact with the second receptor 404 to from a second set of element-receptor complexes; the second fraction excluding the elements of the first fraction.

Elution is conducted by injecting an eluate in the first flow channel 202 and collecting a pool of all elements of the library that are bound to the first receptor 402 or to the second receptor 404.

During the elution of elements that are bound to the first receptor 402, a valve (not shown) can be used to prevent the eluate from interacting with the second receptor 404. Similarly, during the elution of elements that are bound to the second receptor 404, a valve (not shown) can be used to prevent the eluate from interacting with the first receptor 402.

Figure 5A:
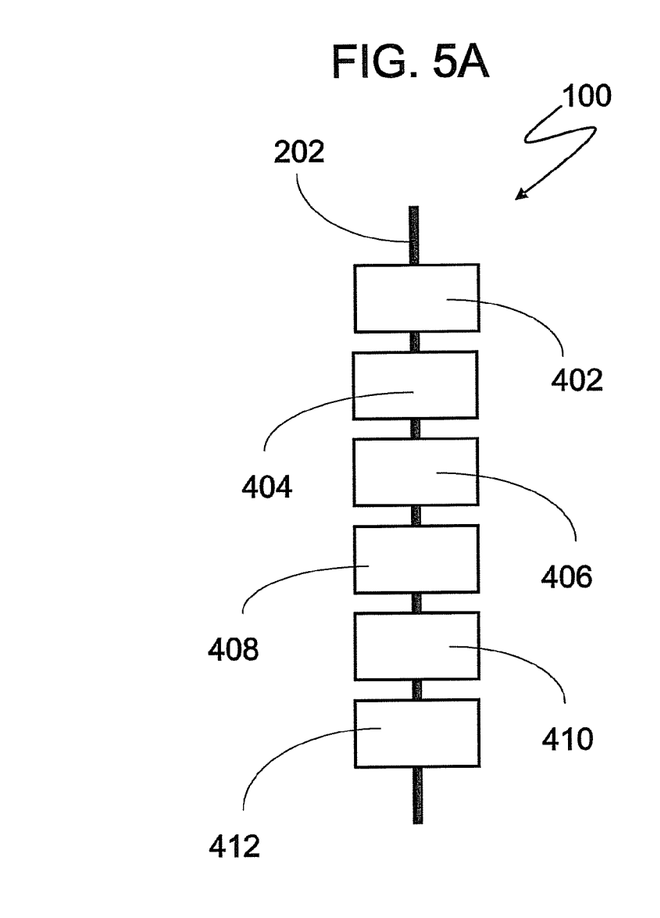
FIGS. 5A and 5B depict other embodiments of the microfluidic device so as to detect elements of a library that can bind to several (FIG. 5A) receptors in the OR mode, or to numerous (FIG. 5B) receptors in the OR mode.
Figure 5B:
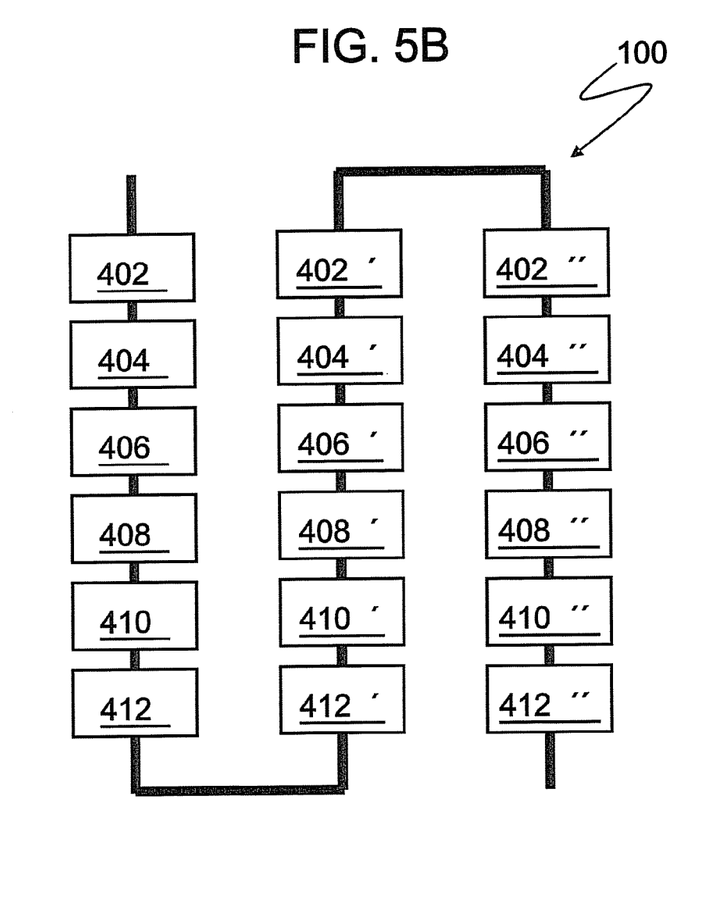

Another method for implementing the OR screening is to pattern multiple receptors along a flow channel as is shown in FIGS. 5A and 5B. The two methods described in FIG. 5 are particularly advantageous for the parallel screening of a many receptors (FIG. 5A) and even a very large number of receptors (FIG. 5B). With reference now to the FIG. 5A, the microfluidic device 100 comprises a series of receptors 402, 404, 406, 408, 410 and 412 that are disposed upon the flow channel 202. Upon introducing a library into the microfluidic device, elements that do not bind to the receptor 402, will move down the flow channel and bond to one of the succeeding receptors 404, 406, 408, 410 or 412. By using eluate solutions that have different properties, the respective elements that are bonded to the different receptors can be sequentially eluted and analyzed.

The methods disclosed above can be advantageously used to screen a large number of elements from a library within a very short period of time. This method of logical screening permits the screening of multiple libraries. The use of logical screening allows for an understanding of the relationship between libraries.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention.

What is claimed is:

1. A non-electrophoretic microfluidic device comprising:
   a chip;
   an entry port, an exit port and a plurality of microfluidic flow channels disposed in said chip, said entry port being in communication with a loading pad also disposed in said chip;
   said loading pad being in fluid communication with said entry port;
   said plurality of microfluidic flow channels forming a linear path being in fluid communication with said entry port and said exit port, said plurality of microfluidic flow channels operative to permit the flow of a library selected from the group consisting of bacteriophages and viruses from said entry port to said exit port, and said microfluidic flow channels being in communication with one another at a junction;
   said microfluidic flow channels being closed systems and said fluid flow within being laminar;
   said exit port, disposed in said chip, has an opening on a face of said chip that is opposed to a face upon which said flow channels are disposed;
   said exit port also has a lip disposed thereon in fluid communication with a pump;
   said pump, in the absence of an electric field, is positioned in said microfluidic device and is adapted to transport a solution via said loading pad through said entry port into said flow channel and out said exit port at said lip;
   a metal layer, disposed, in contact with said chip, said metal layer said loading pad, said entry port, said flow channel and said exit port, all contact said library;
   a passivation layer disposed upon said metal layer;
   said plurality of flow channels in said microfluidic network comprising a first flow channel, a second flow channel and a third flow channel respectively, each of said respective flow channels being controlled by valves;
   said second flow channel and said third flow channel being in fluid communication with and located downstream of said first flow channel;
   said second flow channel and said third flow channel being branches of said first flow channel, said branches being formed at a first junction;

said flow through said first flow channel, said second flow channel and said third flow channel being controlled by a first valve, a second valve and a third valve respectively, said valves disposed either on or off said chip;

an elastomeric substrate disposed on said chip to prevent leakage, said substrate operative to act as an upper wall for said plurality of flow channels, and being operative to seal said flow channel, said entry port and said exit port;

a first receptor and a second receptor disposed on said substrate that are also disposed on said chip;

said first receptor is disposed on said first flow channel, and said second receptor is disposed on said second flow channel;

said first receptor forming an element-receptor complex after exposure to a first solution to binding elements in said library, said first junction being the source of all non-binding elements on said library solution that is diverted to said third flow channel, said non-binding elements not interacting with said second receptor;

said first receptor and said second receptor being selected from the group consisting of an enzyme, a peptide, a protein, an inorganic particle, a cell, a glycan, a viral particle, an antibody, an antigen or a combination comprising at least one of the foregoing receptors any of which can have a ligand-receptor type of interaction with proteins or peptides displayed by bacteriophages;

said bacteriophages adapted to bind said first and second receptors in a flow channel;

wherein said first junction is configured to direct non-binding elements of said library with respect to said first receptor to said third flow channel, and to direct eluted elements bound to said first receptor to said second flow channel, thereby facilitating what results in a mode of screening that determines library elements that bind to both said first receptors and said second receptors.

2. The microfluidic device of claim 1, wherein the receptors comprise an enzyme, a peptide, a protein, an inorganic particle, a cell, a glycan, a viral particle, a polymer, an antibody, an antigen, or a combination comprising at least one of the foregoing receptors.

3. A non-electrophoretic microfluidic device comprising:
a chip;
an entry port, an exit port and five microfluidic flow channels disposed in said chip, said entry port being in communication with a loading pad also disposed in said chip;
said microfluidic five flow channels operative to permit the flow of a library selected from the group consisting of bacteriophages and viruses from said entry port to said exit port,
said microfluidic five flow channels being in serial communication at a junction;
said five microfluidic flow channels being closed systems and said fluid flow within being laminar;
said five microfluidic flow channels being in fluid communication with said entry port and said exit port, said five flow channels operative to permit the flow of said library from said entry port to said exit port;
said exit port disposed in said chip, creates an opening on a face of said chip that is opposed to a face upon which said five flow channels are disposed;
said exit port also having a lip disposed thereon in fluid communication with a pump;
said pump, positioned in said microfluidic device, in the absence of an electric field, is adapted to transport a solution via said loading pad through said entry port into said five flow channels and out saw exit port at said up;

a metal layer contacting structures disposed in said chip, said disposed structures being in contact with said library, said disposed structures consisting of said metal layer, said loading pad, said entry port, said flow channel and said exit port;

a passivation layer disposed upon said metal layer;

said five flow channels comprising a first flow channel, a second flow channel, a third flow channel, a fourth flow channel and a fifth flow channel respectively;

said five flow channels being in fluid communication with said entry port and said exit port, said plurality of flow channels operative to permit the flow of said library from said entry port to said exit port;

said first flow channel, said third flow channel and said fourth flow channel being in fluid communication with one another being joined at a first junction;

said second flow channel, said third flow channel, said fourth flow channel and said fifth flow channel are each downstream of said first flow channel;

said second flow channel, said third flow channel and said fifth flow channel are in fluid communication with one another and meet at a second junction;

an elastomeric substrate disposed upon said chip to prevent leakage, said substrate being operative to act as an upper wall for said plurality of flow channels, and being operative to seal said flow channel, said entry port and said exit port;

a first receptor and a second receptor are each disposed on said chip and are patterned at their respective surfaces;

said first receptor is disposed on said first flow channel, and said second receptor is disposed on said fifth flow channel;

said first receptor and said second receptor being selected from the group consisting of an enzyme, a peptide, a protein, an inorganic particle, a cell, a glycan, a viral particle, an antibody, an antigen or a combination comprising at least one of the foregoing receptors any of which can have a ligand-receptor type of interaction with proteins or peptides displayed by bacteriophages;

said bacteriophages adapted to bind said first and said second receptors in a flow channel;

said second flow channel, said third flow channel and said fourth flow channel are devoid of receptors;

said microfluidic device forming a first element-receptor complex resulting from a first fraction of library elements from said first flow channel interacting with said first receptor, and forming a second element-receptor complex resulting from a second fraction of library elements from said fifth flow channel interacting with said second receptor;

valves are disposed with respect to said chip, a first said valve being located at said first junction and a second said valve being located at said second junction to control flow of said first element-receptor complex through respective flow channels, said first valve and said second valve adapted to prevent library elements that are bound to said first receptor from interacting with said second receptor, thereby preventing any elements or solutions in said first flow channel from interacting with elements or solutions in said second flow channel;

wherein said first junction is configured to direct non-binding elements of said library with respect to said first receptor to said second receptor, via said third flow channel and said fifth flow channel, and to direct eluted elements bound to said first receptor away from said second receptor via said fourth flow channel, thereby facilitating a mode of screening that determines library elements that bind to second receptor but do not bind to said first receptor.

4. A non-electrophoretic microfluidic device comprising:

a chip;

an entry port, an exit port and a first flow channel disposed in said chip, said first flow channel, which contains a library, selected from the group consisting of bacteriophages and viruses, divides at a first junction into two separate flow channels comprising a second flow channel and a third flow channel, each said second flow channel and said third flow channel contain equal proportions of said library;

said entry port being in communication with a loading pad is also disposed in said chip;

said exit port, disposed in said chip, provides an opening on a face of said chip that is opposed to a face upon which said flow channel is disposed;

said exit channel also having a lip disposed thereon in fluid communication with a pump;

said pump, being positioned in said microfluidic device, in the absence of an electric field is adapted to transport a solution via said loading pad through said entry port into said five flow channels and out said exit port at said lip;

said second flow channel has a first receptor disposed thereon;

said third flow channel has a second receptor disposed thereon;

said first receptor and said second receptor are patterned on surfaces that contact elements of said library;

said first receptor and said second receptor being selected from the group consisting of an enzyme, a peptide, a protein, an inorganic particle, a cell, a glycan, a viral particle, an antibody, an antigen or a combination comprising at least one of the foregoing receptors any of which can have a ligand-receptor type of interaction with proteins or peptides displayed by bacteriophages;

said bacteriophages adapted to bind said first and second receptors in a flow channel;

said second flow channel having a first flow controlling device in place between said first junction and said first receptor;

a third flow channel having a second flow controlling device in place between said first junction and said second receptor;

said second flow controlling device and said a third flow controlling device suitable for controlling a fraction of said library that is directed toward said first receptor and toward said second receptor;

said second flow channel and said third flow channel merging at a second junction back into a single fourth flow channel downstream of said second flow channel and said third flow channel;

a metal layer contacting disposed structures, said disposed structures being in contact with a said library, said disposed structures consisting of said metal layer, said loading pad, said entry port, said flow channel and said exit port;

a passivation layer disposed upon said metal layer;

elements bound to said first receptor are prevented from interacting with said second receptor by a first valve in place in said second flow channel; and elements bound to said second receptor are prevented from interacting with said first receptor by a second valve in place in said third flow channel;

wherein said fourth flow channel is in fluid communication with both said second flow channel and said third flow channel, at said second junction downstream from said first receptor and said second receptor, facilitates a mode of screening that determines library elements that bind either to said first receptor or to said second receptor.

* * * * *